(12) United States Patent
Clements et al.

(10) Patent No.: US 10,322,154 B2
(45) Date of Patent: Jun. 18, 2019

(54) SANDALWOOD OIL AND ITS USES RELATED TO CLOSTRIDIUM INFECTIONS

(71) Applicant: Santalis Pharmaceuticals, Inc., San Antonio, TX (US)

(72) Inventors: Ian Clements, San Antonio, TX (US); Paul Castella, San Antonio, TX (US); Corey Levenson, San Antonio, TX (US)

(73) Assignee: SANTALIS PHARMACEUTICALS, INC., San Antonio, TX (US)

( * ) Notice: Subject to any disclaimer, the term of this patent is extended or adjusted under 35 U.S.C. 154(b) by 69 days.

(21) Appl. No.: 15/405,921

(22) Filed: Jan. 13, 2017

(65) Prior Publication Data

US 2017/0128509 A1    May 11, 2017

Related U.S. Application Data

(62) Division of application No. 14/373,810, filed as application No. PCT/US2013/022743 on Jan. 23, 2013, now Pat. No. 9,579,354.

(60) Provisional application No. 61/589,601, filed on Jan. 23, 2012.

(51) Int. Cl.
| | |
|---|---|
| *A61K 36/48* | (2006.01) |
| *A61K 36/185* | (2006.01) |
| *A01N 65/08* | (2009.01) |
| *A61K 45/06* | (2006.01) |

(52) U.S. Cl.
CPC ............ *A61K 36/185* (2013.01); *A01N 65/08* (2013.01); *A61K 45/06* (2013.01); *Y02A 50/469* (2018.01)

(58) Field of Classification Search
CPC ...................................... A61K 36/48

USPC .......................................... 424/776
See application file for complete search history.

(56) References Cited

U.S. PATENT DOCUMENTS

| | | | |
|---|---|---|---|
| 2008/0058413 A1 | 3/2008 | Singh et al. | |
| 2013/0224164 A1* | 8/2013 | Tatarowicz | ........ A61K 31/7048 424/93.41 |

FOREIGN PATENT DOCUMENTS

| | | |
|---|---|---|
| JP | 10505358 | 5/1998 |
| JP | 2006124296 | 5/2006 |
| JP | 2008505621 | 2/2008 |
| WO | 9607430 | 3/1996 |
| WO | 2006003426 | 1/2006 |
| WO | 2009014781 | 1/2009 |
| WO | 2011109411 | 9/2011 |
| WO | 2011130650 | 10/2011 |
| WO | 2011146624 | 11/2011 |

OTHER PUBLICATIONS

Burdock et al. (Food and Chemical Toxicology vol. 46, (2008), pp. 421-432) (Year: 2008).*

(Continued)

*Primary Examiner* — Christopher R Tate
*Assistant Examiner* — Deborah A Davis
(74) *Attorney, Agent, or Firm* — Kilpatrick Townsend & Stockton LLP

(57) ABSTRACT

Provided herein are methods of using therapeutically effective compositions of sandalwood oil to treat, prevent or reduce the recurrence of *Clostridium* infections.

6 Claims, 1 Drawing Sheet

(56) References Cited

OTHER PUBLICATIONS

Jirovetz et al. (Flavour and Fragrance Journal, 2006:21, pp. 465-468). (Year: 2006).*
Database WPI Week 200636 Thomson Scientific, London, GB; AN 2006-347100 XP002707361, & JP 2006 124296 A.
U.S. Appl. No. 14/373,810, "Non-Final Office Action", dated Mar. 24, 2016, 8 pages.
U.S. Appl. No. 14/373,810, "Notice of Allowance", dated Nov. 7, 2016, 9 pages.
AU2013212264, "First Examiner Report", dated Nov. 11, 2016, 4 pages.
Burdock et al., "Safety Assessment of Sandalwood Oil (*Santalum album* L.)", Food and Chemical Toxicology, vol. 46, 2008, pp. 421-432.
Cohen et al., "Clinical Practice Guidelines for Clostridium difficile Infection in Adults: 2010 Update by the Society for Healthcare Epidemiology of America (SHEA) and the Infectious Diseases Society of America (IDSA)", Infection Control and Hospital Epidemiology, vol. 31, May 2010, pp. 431-455.
EP13741240.9 , "Extended European Search Report", dated Jul. 3, 2015, 8 pages.
*EP13741240.9 , "Office Action", dated Mar. 8, 2017, 7 pages.
Hussain et al., "In Vitro Screening of Methanol Plant Extracts for Their Antibacterial Activity", Pak. J. Bot., 43(1), Feb. 2011, pp. 531-538.
Jirovetz et al., "Comparative study on the antimicrobial activities of different sandalwood essential oils of various origin", Flavour and Fragrance Journal, vol. 21 No. 3, May-Jun. 2006, pp. 465-468.
*JP2014-553530, "Notice of Allowance", dated Mar. 27, 2017, 3 pages.
JP2014-553530, "Office Action", dated Aug. 16, 2016, 7 pages.
Misra et al., "Comparative phytochemical analysis and antibacterial efficacy of in vitro and in vivo extracts from East Indian sandalwood tree (*Santalum album* L.)", Lett Appl Microbiol.55(6), Dec. 2012, pp. 476-486.
Ochi et al., "Anti-Helicobacter pylori compounds from Santalum album", J Nat Prod; 68(6), Jun. 2005, pp. 819-824.
PCT/US2013/022743, "International Preliminary Report on Patentability", 5 pages.
PCT/US2013/022743, "International Search Report & Written Opinion", dated May 30, 2013, 7 pages.
Warnke et al., "The Battle Against Multi-Resistant Strains: Renaissance of Antimicrobial Essential Oils as a Promising Force to Fight Hospital-Acquired Infections", Journal of Cranio-Maxillofacial Surgery, vol. 37, 2009, pp. 392-397.

* cited by examiner

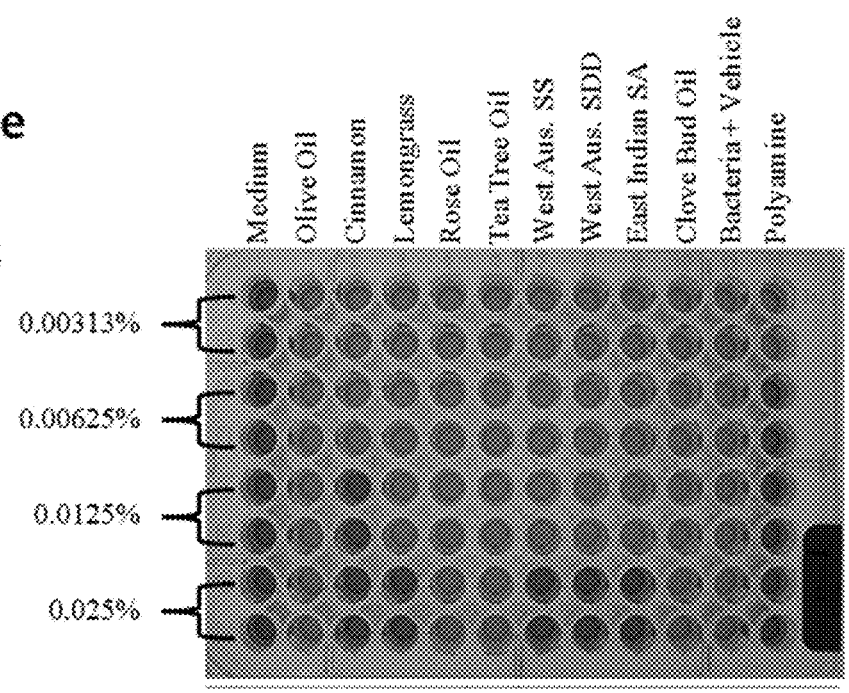

SANDALWOOD OIL AND ITS USES RELATED TO CLOSTRIDIUM INFECTIONS

RELATED APPLICATIONS

This application is a divisional of U.S. patent application Ser. No. 14/373,810, filed on Jul. 22, 2014, which is a U.S. national stage application under 35 U.S.C. § 371 of International Application No. PCT/US2013/022743, filed on Jan. 23, 2013, which claims the benefit of U.S. Provisional Patent Application No. 61/589,601, filed on Jan. 23, 2012, all of which are incorporated by reference herein in their entireties.

SUMMARY

Provided herein are methods of using therapeutically effective compositions of sandalwood oil to treat *Clostridium* infections. More specifically, provided herein is a method of treating or preventing a *Clostridium* infection in a subject. The method comprises administering to the subject a composition including a therapeutically effective amount of sandalwood oil, wherein the subject has a *Clostridium* infection or is at risk of developing a *Clostridium* infection.

Further provided is a method of reducing the recurrence of a *Clostridium* infection in a subject. The method comprises administering to the subject a composition including a therapeutically effective amount of sandalwood oil, wherein the subject is at risk for recurrence of a *Clostridium* infection.

DESCRIPTION OF DRAWING

FIG. 1 is a comparison of *Clostridium difficile* (*C. difficile*) inhibiting activity of sandalwood oils as compared to other oils. Light gray wells indicate bacterial growth. Dark gray wells indicate no bacterial growth. FIG. 1 shows that West Australian sandalwood oil and East Indian sandalwood oil are effective inhibitors of *C. difficile*.

DETAILED DESCRIPTION

In the present methods, oil from any member of the genus *Santalum* can be used. For example, and not to be limiting, East Indian sandalwood (*Santalum album*) or West Australian sandalwood (*Santalum spicatum*) can be utilized in the methods set forth herein. Several other species of the genus also have fragrant wood and are found across India, Australia, Indonesia, and the Pacific Islands. For example, *Santalum ellipticum, S. freycinetianum*, and *S. paniculatum*, the Hawaiian sandalwoods, can also be used.

By way of example, *Santalum spicatum* (West Australian sandalwood) can be used. Other species produced in Australia that can be utilized in the methods and compositions set forth herein include, but are not limited to, *S. acuminatum, S. lanceolatum, S. murrayanum, S. obtusifolium* and *S. album*. The compositions set forth herein can comprise one or more sandalwood oils. The oil(s) can be from one or more members of the genus *Santalum*. In the compositions set forth herein, the sandalwood oil can be a sandalwood heartwood oil, a sandalwood nut oil, or a combination of both.

The components of *S. spicatum* and *S. album* species are different. A comparison of the components of steam distilled Australian and Indian sandalwood heartwood oils is presented in Table 1. The components and their percentages can vary with the extraction method.

TABLE 1

Typical Sandalwood Heartwood Oil Profiles

| Compound | S. spicatum % | S. album % |
|---|---|---|
| E nerolidol | 2.1% | 0.1% |
| Alpha-santalene | nd | 0.5% |
| Cis-alpha-(trans) bergamotene | nd | 0.7% |
| Epi-beta-santalene | nd | 1.1% |
| Beta-santalene | nd | 0.3% |
| Gamma-curcumene | nd | 0.2% |
| Dendrolasin | 1.2% | 0.2% |
| Alpha-santalol | 17.2% | 48.7% |
| Beta-bisabolol | 2.3% | 0.5% |
| Epi-alpha-bisabolol | 8% | nd |
| Z-alpha trans-bergamotol | 4.2% | 2.4% |
| Epi beta-santalol | 1.2% | 5% |
| Cis-beta-santalol | 11.4% | 20.4% |
| E,E, farnesol | 6.5% | nd |
| Cis nuciferol | 13.5% | 0.6% |
| Z-beta-curcumen-12-ol | 7.9% | 0.2% |
| cis lanceol | 2.9% | 1.5% |

The sandalwood heartwood oil can be prepared by steam distillation, supercritical $CO_2$ extraction, solvent extraction, hydro-distillation and combinations thereof. The sandalwood heartwood oil can also be double distilled. It is also possible to synthesize one or more of the active ingredients of sandalwood heartwood oil, as identified in Table 1 and thereafter combine individual active ingredients together.

As used herein, a sandalwood heartwood oil can be a sandalwood heartwood oil that conforms with International Organization for Standardization (ISO) specifications for the oil and therefore comprises 20-45% santalols, when derived from *S. spicatum*, and 57-79% santalols when derived from *S. album*. However, the 20-45% santalols from *S. spicatum* and the 57-79% santalols from *S. album* are determined against the pure oil and before such oil is combined with any other solvents, excipients or active ingredients. It is understood that an efficacious preparation of sandalwood heartwood oil may have a concentration of santalols lower (or higher) than the sandalwood heartwood oil it is prepared from and that the efficacious concentrations may be derived from sandalwood heartwood oils that are outside of the ISO specification prior to formulation. A santalol can be an α-santalol (shown below), a β-santalol (shown below), or any other active isomers or derivatives (such as esters) thereof.

As used herein, a sandalwood heartwood oil can comprise at least about 20%, 25%, 30%, 35%, 40%, 45%, 50%, 55%, 60%, 65%, 70%, 75%, 80%, 85%, 90%, 95%, 99% santalols or any percentage in between the percentages set forth herein, when derived from *S. spicatum*. The sandalwood heartwood oil can comprise at least 45%, 50%, 55%, 60%, 65%, 70%, 75%, 80%, 85%, 90%, 95%, 99% santalols or any percentage in between the percentages set forth herein, when derived from *S. album*. As set forth above, the oil can be extracted from cultivated trees or from cell culture of tree cells.

In the methods and compositions set forth herein, the sandalwood heartwood oil can comprise the ingredients in the amounts listed in Table 1 plus or minus about 20%, and more preferably plus or minus about 10%, 5%, 2%, 1% or any percentage in between the percentages set forth herein.

It is also understood that the activity of sandalwood heartwood oil can be due to one or more components set forth in Table 1 acting either separately or together. Therefore, formulations that increase the concentration of the active component(s) and reduce the concentration of the inactive component(s) are set forth herein. Synthetic versions of the active components, or their derivatives, may be formulated in conjunction with or to replace the naturally occurring components of sandalwood heartwood oil. Compositions comprising purified or synthetic versions of an active component or derivative thereof can also be utilized in the methods set forth herein. For example, a composition comprising alpha-santalol (shown below) or beta-santalol (shown below) can be utilized to treat, prevent or reduce the recurrence of a *Clostridium* infection.

alpha-santalol beta-santalol

In the methods and compositions set forth herein, sandalwood nut oil can be from the nut of any member of the genus *Santalum*. For example, and not to be limiting, East Indian sandalwood (*Santalum album*) or West Australian sandalwood (*Santalum spicatum*) nut oil can be utilized in the methods and compositions set forth herein. Nut oil from *Santalum ellipticum*, *S. freycinetianum*, and *S. paniculatum*, the Hawaiian sandalwoods, can also be used. Typical analytical values for sandalwood nut oil are as follows:

| Fatty Acid | % concentration |
| --- | --- |
| Palmitic (C16.0) | 3.5% |
| Stearic (C18.0) | 1.6% |
| Oleic (C18.1 c-9) | 50.7% |
| Linoleic (C18.2 c-9 12) | 1.1% |
| Linolenic (C18.3 c-9, 12, 15) | 4.6% |
| Gondoic (C20.1 c-11) | 3% |
| Ximenynic | 35.8% |

The therapeutically effective amount of sandalwood oil utilized in the compositions set forth herein can be, for example, a concentration greater of about 0.2% (w/w) and up to about 100% (w/w). For example, the therapeutically effective amount can be about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 15%, 20%, 25%, 30%, 35%, 40%, 45%, 50%, 55%, 60%, 65%, 70%, 75%, 80%, 85%, 90%, 95%, 100% or any percentage (w/w) in between the percentages set forth herein.

As set forth above, the compositions set forth herein can comprise sandalwood heartwood oil, sandalwood nut oil or a combination of both. Therefore, the sandalwood oil can comprise only sandalwood heartwood oil, wherein the concentration of the sandalwood heartwood oil is from about 0.2% to about 100% (w/w). For example, the concentration of sandalwood heartwood oil can be about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 15%, 20%, 25%, 30%, 35%, 40%, 45%, 50%, 55%, 60%, 65%, 70%, 75%, 80%, 85%, 90%, 95%, 100% or any percentage (w/w) in between the percentages set forth herein.

The sandalwood oil can also comprise only sandalwood nut oil, wherein the concentration of the sandalwood nut oil is from about 0.2% to about 100% (w/w). For example, the concentration is sandalwood nut oil can be about 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 15%, 20%, 25%, 30%, 35%, 40%, 45%, 50%, 55%, 60%, 65%, 70%, 75%, 80%, 85%, 90%, 95%, 100% or any percentage (w/w) in between the percentages set forth herein.

The sandalwood oil can also comprise a combination of sandalwood heartwood oil and sandalwood nut oil, wherein the concentration of the sandalwood heartwood oil and the concentration of the sandalwood nut oil can each range from about 0.2% to about 99.8%, and the combined concentrations do not exceed 100% (w/w).

Provided herein is method of treating or preventing a *Clostridium* infection in a subject. The method comprises administering to the subject a composition with a therapeutically effective amount of sandalwood oil, wherein the subject has a *Clostridium* infection or is at risk of developing a *Clostridium* infection Further provided is a method of reducing the recurrence of a *Clostridium* infection in a subject. The method comprises administering to the subject a composition including a therapeutically effective amount of sandalwood oil, wherein the subject is at risk for recurrence of a *Clostridium* infection

*Clostridium* is a genus of rod-shaped Gram-positive bacteria capable of producing endospores. The methods set forth herein can be used to treat the vegetative as well as the spore form of any *Clostridium* infection. Several *Clostridium* species are responsible for disease in humans. These include, but are not limited to, *Clostridium difficile* (*C. difficile*), *Clostridium botulinum* (*C. botulinum*),

*Clostridium perfringens* (*C. perfringens*), *Clostridium tetani* (*C. tetani*) and *Clostridium sordelli* (*C. sordelli*).

*C. difficile* is the most serious cause of antibiotic-associated diarrhea and can lead to pseudomembranous colitis, a severe inflammation of the colon, often resulting from eradication of the normal gut flora by antibiotics. In a very small percentage of the adult population, *C. difficile* bacteria naturally reside in the gut. Other people accidentally ingest spores of the bacteria while they are patients in a hospital, nursing home, or similar facility. When the bacteria are in a colon in which the normal gut flora has been destroyed, for example, after a broad-spectrum antibiotic has been used, the gut becomes overrun with *C. difficile*. This overpopulation is harmful because the bacteria release toxins that can cause bloating, diarrhea and abdominal pain.

*C. botulinum* produces neurotoxins that cause the flaccid muscular paralysis seen in botulism.

*C. perfringens* is a common cause of food-borne illness, with poorly prepared meat and poultry the main culprits in harboring the bacterium. The *clostridium* perfringens enterotoxin (CPE) mediating the disease is heat-labile (inactivated at 74° C.) and can be detected in contaminated food, if not heated properly, and feces. Incubation time is between 6 and 24 (commonly 10-12) hours after ingestion of contaminated food. Often, meat is well prepared, but too far in advance of consumption. Since *C. perfringens* forms spores that can withstand cooking temperatures, if let stand for long enough, germination ensues and infective bacterial colonies develop. Symptoms typically include abdominal cramping and diarrhea; vomiting and fever are unusual.

*C. tetani* usually enters a host through a wound to the skin and then it replicates. Once an infection is established, *C. tetani* produces two exotoxins, tetanolysin and tetanospasmin. Tetanospasmin released in the wound is absorbed into the circulation and reaches motor nerves all over the body. The toxin acts at several sites within the central nervous system including nerve terminals in the spinal cord, brain, peripheral nerves and autonomic nervous system. The clinical manifestations of tetanus are caused when tetanus toxin blocks inhibitory impulses, by interfering with the release of neurotransmitters. These inhibitory neurotransmitters inhibit the alpha motor neurons. With diminished inhibition, the resting firing rate of the alpha motor neuron increases, producing rigidity, unopposed muscle contraction and spasm. Characteristic features are risus sardonicus (a rigid smile), trismus (commonly known as "lock-jaw"), and opisthotonus (rigid, arched back). Seizures may occur, and the autonomic nervous system may also be affected. Hypertension and tachycardia alternating with hypotension and bradycardia may develop.

The *Clostridium* infection can be in the digestive tract, for example, in the stomach, small intestine, lower intestine or colon of a subject. The infection can also be in the central or peripheral nervous system or autonomic nervous system of a subject. A *Clostridium* infection can also be in the urinary tract of a subject. All strains are contemplated herein. A decrease or reduction of infection can occur in vitro, ex vivo or in vivo.

As utilized throughout, the term "infection" encompasses all phases of the *Clostridium* life cycle including, but not limited to, replication, spore formation, transition from a spore form of the bacteria to a vegetative form of the bacteria, toxin production and receptor-mediated cell entry of toxins.

As used herein, the term subject can be a vertebrate, more specifically a mammal (e.g., a human, horse, pig, rabbit, dog, sheep, goat, non-human primate, cow, cat, guinea pig or rodent), a bird, a reptile or an amphibian. The term does not denote a particular age or sex. Thus, adult and newborn subjects, whether male or female, are intended to be covered. As used herein, patient or subject may be used interchangeably and can refer to a subject with a disease or disorder. The term patient or subject includes human and veterinary subjects.

As used herein the terms treatment, treat, treating or ameliorating refers to a method of reducing one or more signs or symptoms of the disease or condition. Thus in the disclosed method, treatment can refer to a 10%, 20%, 30%, 40%, 50%, 60%, 70%, 80%, 90%, or 100% reduction or amelioration in the severity of an established disease or condition, as evidenced by a reduction in one or more signs or symptoms of the disease or condition. For example, and not to be limiting, a method for treating a *Clostridium* infection is considered to be a treatment if there is a 10% reduction in one or more signs or symptoms of the infection in a subject as compared to control. For example, the method for treating a *Clostridium* infection is considered to be a treatment if there is a 10% reduction in one or more signs or symptoms of the *Clostridium* infection in a subject as compared to a control subject that did not receive a composition comprising sandalwood oil described herein. Thus the reduction can be a 10, 20, 30, 40, 50, 60, 70, 80, 90, 100%, or any percent reduction in between 10 and 100 as compared to control levels. It is understood that treatment does not necessarily refer to a cure or complete ablation of the disease, condition, or symptoms of the disease or condition.

A subject can also harbor *Clostridium* resulting in carriage of the bacteria, which can be asymptomatic. For example, the subject can harbor *Clostridium* spores that can germinate to become active, vegetative cells. Thus, also provided herein is a method of reducing *Clostridium* carriage comprising administering to the subject a composition comprising a therapeutically effective amount of sandalwood oil, wherein the subject is a carrier or is at risk of becoming a carrier for *Clostridium*. In this method, a reduction in spore formation, a reduction in the number of spores and/or a reduction in the number of spores that germinate to become active, vegetative cells can occur. The reduction can be a 10%, 20%, 30%, 40%, 50%, 60%, 70%, 80%, 90%, or 100% reduction as compared to a control.

Further provided is a method of reducing the infectivity of *Clostridium* spores, comprising contacting a population of *Clostridium* spores with an effective amount of sandalwood oil. In this method, the number of spores and/or the number of spores that germinate to become active, vegetative cells can be reduced. The reduction can be a 10%, 20%, 30%, 40%, 50%, 60%, 70%, 80%, 90%, or 100% reduction as compared to a control.

The population of spores can be an in vivo population or an in vitro population.

As utilized herein, by reducing the recurrence of a *Clostridium* infection is meant a method of preventing, precluding, delaying, averting, obviating, forestalling, stopping, or hindering the onset, incidence or severity of the reappearance of a *Clostridium* infection in a subject. As utilized herein, by reappearance of a *Clostridium* infection is meant the reappearance of one or more signs or clinical symptoms of a *Clostridium* infection after a period devoid of one or more clinical symptoms of a *Clostridium* infection. The recurrence of a *Clostridium* infection can be after treatment for a *Clostridium* infection, for example, after treatment of *C. difficile* with vancomycin, metronidazole and or fidaxomicin. The recurrence of a *Clostridium* infection can also be after a remission. A recurrence can occur days, weeks, months or years after treatment or after a remission. For example, the disclosed method is considered to reduce the occurrence of a *Clostridium* infection if there is a reduction or delay in onset, incidence or severity of the reappearance of a *Clostridium* infection, or one or more symptoms of a *Clostridium* infection in a subject at risk for a recurrence of a *Clostridium* infection compared to control subjects at risk for a recurrence of a *Clostridium* infection that did not receive a composition comprising sandalwood oil disclosed herein. The disclosed method is also considered to reduce the recurrence of a *Clostridium* infection if there is a reduction or delay in onset, incidence or severity of the reappearance of a *Clostridium* infection, or one or more symptoms of a *Clostridium* infection in a subject at risk for recurrence of a *Clostridium* infection after receiving a composition comprising sandalwood oil disclosed herein as compared to the subject's progression prior to receiving treatment. Thus, the reduction or delay in onset, incidence or severity of recurrence of a *Clostridium* infection can be about a 10, 20, 30, 40, 50, 60, 70, 80, 90, 100%, or any amount of reduction in between.

In the methods set forth herein, a composition comprising a therapeutically effective amount of sandalwood oil can selectively inhibit *Clostridium* infection in the subject. By selective inhibition is meant that inhibition of *Clostridium* infection occurs while maintaining substantial survival of the natural flora in the digestive tract of the subject.

For the administration methods disclosed herein, each method can optionally comprise the step of diagnosing a subject with a *Clostridium* infection or at risk of developing a *Clostridium* infection. The method can also include assessing the effectiveness of the sandalwood oil composition and modifying the treatment regimen.

The compositions set forth herein can be provided in a pharmaceutical composition. The compositions include a therapeutically effective amount of the sandalwood oil in combination with a pharmaceutically acceptable carrier and, in addition, may include other medicinal agents, pharmaceutical agents, carriers, or diluents. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. By pharmaceutically acceptable is meant a material that is not biologically or otherwise undesirable, which can be administered to an individual along with sandalwood oil without causing unacceptable biological effects or interacting in a deleterious manner with the other components of the pharmaceutical composition in which it is contained.

The compositions comprising a therapeutically effective amount of sandalwood oil can be concurrently administered with another pharmaceutical agent or agents. The pharmaceutical agent can be formulated with the therapeutically effective amount of sandalwood in a single composition or can be formulated in a separate composition. The compositions comprising a therapeutically effective amount of sandalwood oil can also be administered subsequent to or prior to treatment with another pharmaceutical agent. For example, and not to be limiting, a composition comprising a therapeutically effective amount of sandalwood oil can be administered concurrently with, subsequent to, or prior to administration of vancomycin, metronidazole and/or fidaxomicin in order to treat, prevent or reducing the recurrence of *C. difficile*.

Any appropriate route of administration may be employed, for example, administration can be systemic or local. Systemic administration includes administration via injection or infusion. Other routes of administration, such as intranasal, dermal, aerosol, vaginal, rectal or oral administration are also contemplated. By pharmaceutically acceptable carrier is meant a material that is not biologically or otherwise undesirable, which can be administered to an individual along with the selected compound without causing unacceptable biological effects or interacting in a deleterious manner with the other components of the pharmaceutical composition in which it is contained.

Administration can be carried out using therapeutically effective amounts of the compositions described herein for periods of time effective to treat or reduce recurrence of a *Clostridium* infection. The effective amount may be determined by one of ordinary skill in the art and includes exemplary dosage amounts for a mammal of from about 0.5 to about 200 mg/kg of body weight of active composition per day, which may be administered in a single dose or in the form of individual divided doses, such as from 1 to 4 times per day. Such a dosing schedule can continue for days, weeks or months, depending on the subject and the type of infection. Alternatively, the dosage amount can be from about 0.5 to about 150 mg/kg of body weight of active composition per day, about 0.5 to 100 mg/kg of body weight of active composition per day, about 0.5 to about 75 mg/kg of body weight of active composition per day, about 0.5 to about 50 mg/kg of body weight of active composition per day, about 0.5 to about 25 mg/kg of body weight of active composition per day, about 1 to about 20 mg/kg of body weight of active composition per day, about 1 to about 10 mg/kg of body weight of active composition per day, about 20 mg/kg of body weight of active composition per day, about 10 mg/kg of body weight of active composition per day, or about 5 mg/kg of body weight of active composition per day.

According to the methods taught herein, the subject is administered an effective amount of sandalwood oil. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like. As set forth in the Examples, sandalwood oil can be formulated with, for example, polyethylene glycol 8000. This formulation can further comprise hydroxypropyl methylcellulose acetate succinate (HPMCAS-LF). For example, a formulation can comprise from about 40% to about 60% sandalwood oil, polyethylene glycol 8000 and HPMCAS-LF, wherein the polyethylene glycol 8000 and the HPMCAS-LF are present in the formulation in about a 2:1 ratio to about a 10:1 ratio. For example, the percentage of sandalwood oil in a formulation can be about 40, 41, 42, 43, 44, 45, 46, 47, 48, 49, 50, 51, 52, 53, 54, 55, 56, 57, 58, 59 or 60%. The formulation can further comprise polyethylene glycol 8000 and HPMCAS-LF wherein the ration of polyethylene glycol 8000 to HPMCAS-LF is about a 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1 or a 10:1 ratio.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Ranges may be expressed herein as from about one particular value, and/or to about another particular value. When such a range is expressed, this includes from the one particular value and/or to the other particular value. Similarly, when values are expressed as approximations, by use of the antecedent about, it will be understood that the particular value is disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

Example I

Bacterial Cells and Maintenance

Bacterial *C. difficile* culture strains (BAA-1875, 43594, 43596) were obtained from the American Type Culture Collection (ATCC; Manassas, Va.). The *C. difficile* cultures were maintained in a liquid complete growth medium composed of Reinforced Clostridial Medium (RCM) with 0.1% 2-mercaptoethanol (Beta-ME; BME) as a supplement. Cultures were grown in a 37° C. incubator under anaerobic conditions (tightly sealed gas jars with a gas mixture: 80% $N_2$, 10% $CO_2$, 10% $H_2$). For this study, cultures of the indicated organisms were grown for 48 hr in 14 ml snap-cap tubes containing 10 ml complete growth medium. Cultures were still actively growing in log phase and were triturated (in anaerobic gas) until homogeneous cell suspensions were obtained.

Quantified Cell Density

Cell suspensions were diluted 1/10 into RCM in polystyrene cuvettes and $OD_{600}$ readings were measured compared to the RCM blank. For each bacterial strain, a 40 ml suspension of a 0.02 $OD_{600}$ was then made in complete growth medium.

Serial Dilutions and Test Concentrations of Oils

Serial dilutions of test oils were prepared in sterile 15 ml tubes to final 2× concentrations as described in Table 2. Each oil was mixed with 50% glycerol plus 0.1% Tween 80 to a final volume of 1.0 ml at 20× final concentration, then vortexed to create an emulsion. To make a final volume of 10 ml at 2× final concentration, 9 ml of complete growth medium was added.

Each concentration was vortexed before distributing 1 ml of suspension to appropriately pre-labeled 5 ml snap-top culture tubes as per the Sample tube numbers (#1 to #96) shown in Tables 3-5. Control and test concentrations were distributed in duplicates, labeled "a" and "b".

TABLE 2

Formulations, Volumes and Methods

| Final 2X Concentration (%) | Final Volume RCM + Oil (ml) | Volume RCM (ml) | Transfer Volume (ml) | Volume Oil 20X Final Concentr'n (ul) | Volume Glycerol/ Tween 80 (ul) |
|---|---|---|---|---|---|
| 0 | 10 | 9 | 1 | 0.000 | 1000 |
| 0.0625 | 10 | 9 | 1 | 6.25 | 993.75 |
| 0.125 | 10 | 9 | 1 | 12.5 | 987.5 |
| 0.25 | 10 | 9 | 1 | 25 | 975 |
| 0.5 | 10 | 9 | 1 | 50 | 950 |
| 1 | 10 | 9 | 1 | 100 | 900 |
| 2 | 10 | 9 | 1 | 200 | 800 |
| 4 | 10 | 9 | 1 | 400 | 600 |
| Total | 80 | 72 | 8 | 793.75 | 7206.25 |

Inoculation with Test Organisms

The experiment was started by inoculating each of the 96 tubes as follows: 1.0 ml of each stock culture was distributed to the appropriate tubes as indicated (Tables 2-4). Tubes were monitored by visualization of individual tubes for growth, and pictures were taken of each individual tube after 4 days of incubation in complete growth medium alone, or in growth medium containing the test oils as described.

Results

Tables 3-5 summarize the results. *C. difficile* growth was seen in all control tubes by visual examination. However, the 3 species had different growth patterns: BAA-1875 grew as a flocculent mass from the bottom of the tube approximately ¾ up the liquid column, whereas the others grew as a flocculent mass (strain 43594) or more pelleted mass (strain 43596) on the bottom of the tube. All of the test concentrations of both *S. album* and *S. spicatum* oils inhibited growth in all 3 test species of *C. difficile*. Thus sandalwood oil is an effective antimicrobial against these organisms.

TABLE 3

Effects of Santalum species oils on growth of *C. difficile* strain BAA-1875.

| Sample Tube # | Species Oil | Final Test Concentration % | Replicate | Relative Growth |
|---|---|---|---|---|
| 1 | S. album | Control | a | +++ |
| 2 | | Control | b | +++ |
| 3 | | 0.0313 | a | 0 |
| 4 | | 0.0313 | b | 0 |
| 5 | | 0.0625 | a | 0 |
| 6 | | 0.0625 | b | 0 |
| 7 | | 0.125 | a | 0 |
| 8 | | 0.125 | b | 0 |
| 9 | | 0.25 | a | 0 |
| 10 | | 0.25 | b | 0 |
| 11 | | 0.5 | a | 0 |
| 12 | | 0.5 | b | 0 |
| 13 | | 1.0 | a | 0 |
| 14 | | 1.0 | b | 0 |
| 15 | | 2.0 | a | 0 |
| 16 | | 2.0 | b | 0 |
| 17 | S. spicatum | Control | a | +++ |
| 18 | | Control | b | +++ |
| 19 | | 0.0313 | a | 0 |
| 20 | | 0.0313 | b | 0 |
| 21 | | 0.0625 | a | 0 |
| 22 | | 0.0625 | b | 0 |
| 23 | | 0.125 | a | 0 |
| 24 | | 0.125 | b | 0 |
| 25 | | 0.25 | a | 0 |
| 26 | | 0.25 | b | 0 |
| 27 | | 0.5 | a | 0 |
| 28 | | 0.5 | b | 0 |
| 29 | | 1.0 | a | 0 |
| 30 | | 1.0 | b | 0 |
| 31 | | 2.0 | a | 0 |
| 32 | | 2.0 | b | 0 |

TABLE 4

Effects of *Santalum* species oils on growth of *C. difficile* strain 43594.

| Sample Tube # | Species Oil | Final Test Concentration % | Replicate | Relative Growth |
|---|---|---|---|---|
| 33 | S. album | Control | a | +++ |
| 34 | | Control | b | +++ |
| 35 | | 0.0313 | a | 0 |
| 36 | | 0.0313 | b | 0 |
| 37 | | 0.0625 | a | 0 |
| 38 | | 0.0625 | b | 0 |
| 39 | | 0.125 | a | 0 |
| 40 | | 0.125 | b | 0 |
| 41 | | 0.25 | a | 0 |
| 42 | | 0.25 | b | 0 |
| 43 | | 0.5 | a | 0 |
| 44 | | 0.5 | b | 0 |
| 45 | | 1.0 | a | 0 |
| 46 | | 1.0 | b | 0 |
| 47 | | 2.0 | a | 0 |
| 48 | | 2.0 | b | 0 |
| 49 | S. spicatum | Control | a | +++ |
| 50 | | Control | b | +++ |
| 51 | | 0.0313 | a | 0 |
| 52 | | 0.0313 | b | 0 |
| 53 | | 0.0625 | a | 0 |
| 54 | | 0.0625 | b | 0 |

TABLE 4-continued

Effects of Santalum species oils on growth of C. difficile strain 43594.

| Sample Tube # | Species Oil | Final Test Concentration % | Replicate | Relative Growth |
|---|---|---|---|---|
| 55 | | 0.125 | a | 0 |
| 56 | | 0.125 | b | 0 |
| 57 | | 0.25 | a | 0 |
| 58 | | 0.25 | b | 0 |
| 59 | | 0.5 | a | 0 |
| 60 | | 0.5 | b | 0 |
| 61 | | 1.0 | a | 0 |
| 62 | | 1.0 | b | 0 |
| 63 | | 2.0 | a | 0 |
| 64 | | 2.0 | b | 0 |

TABLE 5

Effects of Santalum species oils on growth of C. difficile strain 43596.

| Sample Tube # | Species Oil | Final Test Concentration % | Replicate | Relative Growth |
|---|---|---|---|---|
| 65 | S. album | Control | a | +++ |
| 66 | | Control | b | +++ |
| 67 | | 0.0313 | a | 0 |
| 68 | | 0.0313 | b | 0 |
| 69 | | 0.0625 | a | 0 |
| 70 | | 0.0625 | b | 0 |
| 71 | | 0.125 | a | 0 |
| 72 | | 0.125 | b | 0 |
| 73 | | 0.25 | a | 0 |
| 74 | | 0.25 | b | 0 |
| 75 | | 0.5 | a | 0 |
| 76 | | 0.5 | b | 0 |
| 77 | | 1.0 | a | 0 |
| 78 | | 1.0 | b | 0 |
| 79 | | 2.0 | a | 0 |
| 80 | | 2.0 | b | 0 |
| 81 | S. spicatum | Control | a | +++ |
| 82 | | Control | b | +++ |
| 83 | | 0.0313 | a | 0 |
| 84 | | 0.0313 | b | 0 |
| 85 | | 0.0625 | a | 0 |
| 86 | | 0.0625 | b | 0 |
| 87 | | 0.125 | a | 0 |
| 88 | | 0.125 | b | 0 |
| 89 | | 0.25 | a | 0 |
| 90 | | 0.25 | b | 0 |
| 91 | | 0.5 | a | 0 |
| 92 | | 0.5 | b | 0 |
| 93 | | 1.0 | a | 0 |
| 94 | | 1.0 | b | 0 |
| 95 | | 2.0 | a | 0 |
| 96 | | 2.0 | b | 0 |

Comparison of Sandalwood Oil with Other Oils

Test oils were prepared at 2X final concentration. Briefly, each oil was diluted 1:00 in a sterile solution of 50% glycerol and 0.1% Tween 80 (1% final concentration of oil). This suspension was vortexed vigorously for 10 seconds and then further diluted 1:20 with Proteose Fructose Neutral Red (PFNR) growth indicating medium (0.05% final oil concentration). This working stock was then diluted 2× with PFNR three more times to generate the 4 working concentrations at 2× the final concentration. The glycerol:Tween 80 solution was diluted 1:20 with PFNR followed by 3 more 2× dilutions to be inoculated as vehicle controls. All samples were vortexed between dilutions to ensure homogeneity of the suspension. All work was performed within the anaerobic glovebox to ensure exclusion of oxygen in the test samples and growth medium.

100 µl of each suspension was plated per well in duplicate as described in FIG. 1. 4 replicate plates were made. Bacterial cultures were maintained in PFNR broth in a 35° C. incubator under anaerobic conditions (glovebox 80% $N_2$, 10% $CO_2$, 10% $H_2$). 24 hour cultures of the indicated organisms grown in 14 ml snap-top tubes were pipetted up and down until a homogeneous suspension was obtained. Cell suspensions were diluted 1/10 into PBS in polystyrene cuvettes and $OD_{600}$ readings were measured compared to a PBS blank. 40 ml of a 0.02 $OD_{600}$ suspension was made for each bacterial strain in PFNR. 100 ul of 0.02 $OD_{600}$ cell suspension was plated on top of the wells preloaded with test suspensions. The final volume was 200 ul, with a cell concentration 0.01 $OD_{600}$, and each test suspension at 1× concentration. The first column of each plate contained 200 ul of PFNR only as a negative control.

Plates were covered and then placed into the 35° C. incubator within the glovebox and allowed to incubate overnight. After 14 hours of incubation the plates were removed from the glovebox to photograph and read the absorbance at 450 nm (yellow peak absorbance). The plates were replaced in the glovebox and allowed to incubate further. After a total of 38 hours of incubation the plates were removed from the glovebox again to photograph and the absorbance was read at 450 nm. FIG. 1 shows that both Western Australian sandalwood oil and East Indian sandalwood oil are effective antimicrobial inhibitors of C. difficile.

Example II

Strain

Clostridium difficile NCTC 13366 Ribotype 27 (vegetative bacteria and spores) was used. Vegetative cells of this strain were grown in Brain-Heart Infusion (BHIS) broth and agar and and 0.1% taurocholate. As explained below, the spore form of this strain was grown in BHIS broth and agar without 0.1% taurocholate.

Test Compound Preparation

200 µL of sandalwood oil (test compound) were mixed with 100 µL of DMSO and then combined with 4.7 mL of 0.01% Tween 80 in 7H12. The resulting solution was composed of 4% sandalwood oil and 1% DMSO. Once the compound was assayed, the concentrations of sandalwood oil and DMSO were 2% and 1% respectively.

Minimum Inhibitory Concentration (MIC) Determination

The MIC of the test compound was determined according to CLSI guidelines for the microdilution method. Briefly, the test compound dissolved in appropriate broth growth medium was assayed in triplicate in a 2-fold dilution range from 2% to 0.0001%. A fresh working stock of organism was thawed and diluted to a concentration of approximately $5 \times 10^5$ CFU/mL and then added to all test and negative control wells and incubated for the appropriate time period and conditions. At the end of the incubation period, the test wells were visually scored for the lowest concentration of test or control compound to inhibit growth of the organism.

Spore Inhibition Assay

Taurocholate is necessary for C. difficile spores to transition (germinate) into vegetative bacteria. According to data from the MIC of vegetative C. difficile, the compound is inhibitory across the entire concentration range assayed with the organism in its vegetative state. This made it necessary to exclude taurocholate from the compound exposure portion of the assay. In order to test the inhibition of C. difficile spores to the test compound, exposure was carried out in BHIS broth without taurocholate to eliminate the possibility of spore germination. After a 24 hour exposure, an aliquot from each test well was transferred to BHIS agar plates containing taurocholate to allow the spores to germinate and then produce colonies. The aliquot was spread across the surface of the plate and then incubated for 48 hrs in an anaerobic environment at 37° C. The colonies from each test sample were counted and compared to the number of colonies produced by the negative (untreated) controls. Test samples that resulted in colony counts lower than the negative control samples indicated inhibition of the *C. difficile* spores by the test compound. The number of colonies from the test samples were divided by the number of colonies from the negative control samples and then multiplied by 1.0 to produce a percent inhibition value.

| *Clostridium difficile* NCTC 13366 Spore Inhibition Assay | |
|---|---|
| Test Compound Concentration | Percent inhibition |
| 0.5%-0.0001% | no significant inhibition |
| 1% | ≥50% |
| 2% | ≥99% |

Example III

Formulations

Challenge Preparation: Challenge preparation was performed inside an anaerobe glove box in IW 305 in order to minimize oxygen exposure. A seed stock of the challenge organism (*C. difficile*) was thawed and added to the appropriate growth medium on Day −1. The organism was incubated anaerobically overnight (18-24 hrs) at 37° C. On the day of challenge (Day 0), the culture was diluted in DPBS to achieve a target concentration of $10^4$ CFU/dose. Syringes with attached gavage needles were loaded with challenge material and placed on ice for transfer to the animal group.

Challenge Formulation Storage, Stability, and Handling: The challenge doses were kept on ice or refrigerated until dosing and considered stable throughout the dosing period.

Challenge Dose Formulation Concentration and Homogeneity Analysis: Challenge concentration was determined spectrophotometrically on the day of challenge and confirmed by retrospective plate count.

Polymer Carrier: The polymer carrier used in these studies was a composition comprising polyethylene glycol 8000 (PEG8000) and hydroxypropyl methylcellulose acetate succinate (HPMCAS-LF). HPMCAS-LF was used to make the polymer insoluble at low pH. The formulation comprising a polymer carrier and sandalwood oil comprised about 50% PEG8000, about 41.67% sandalwood oil and about 8.33% HPMCAS-LF.

Test System 60 female C57BL\6 mice that weighed approximately 26-30 grams and were approximately 7-11 weeks old on Day 0 were used. The C57BL/6 mouse is susceptible to *C. difficile* and used extensively as a good animal model for the evaluation of antibacterial therapeutics. Treatments were administered via oral gavage and/or intraperitoneally in order to mimic treatment in humans. The challenge was administered via oral gavage as this is both an effective and minimally invasive route of administration that mimics the natural route of infection.

Animals were housed under A/BSL2 containment conditions upon arrival at Southern Research Institute. Mice were group-housed (up to 5/cage) in micro-isolators. Appropriate bedding was used in the bottom of the cages. Analyses of the bedding, supplied by the vendor, was reviewed by Southern Research's veterinarian, or designee, to ensure that no known contaminants were present that could interfere with or affect the outcome of the study.

Animals were housed in an environmentally monitored, well-ventilated room maintained at a temperature of 68-79° F. (approximately 20-26° C.) and a relative humidity of 30%-70%. Fluorescent lighting provided illumination, approximately 12 hours per day.

Mice were fed certified rodent chow #2016C (Harlan, Inc.; Madison, Wis.) during the pre-study and study periods. Feed was provided ad libitum. Analyses of the feed, provided by the manufacturer, were reviewed by Southern Research's Veterinarian, or designee, to ensure that no known contaminants were present that would be expected to interfere with or affect the outcome of the study.

Water (Birmingham public water supply) was supplied ad libitum during the pre-study and study periods. Samples of water from the animal facility were periodically analyzed, and the analysis was reviewed by Southern Research's Veterinarian, or designee, to assure that no known contaminants are present that would be expected to interfere with or affect the outcome of the study.

Animals were provided a psychological well-being program for social enrichment as approved by the Institutional Animal Care and Use Committee (IACUC). Animals were provided cage modifications and consumable enrichment for their psychological well-being.

Upon arrival, mice were housed in the AIBSL2 facility. Prior to the start of the study, the animals were observed for general health and acceptability for use in this study.

During Week −1, each mouse was uniquely identified by ear punch and an implantable micro-identification device (chip) (IPTT-300 Chip; Biomedic Data Systems Inc.; Seaford, Del.) inserted subcutaneously on the back. The microidentification chip also provided body temperature data. Body temperature was taken rectally if chip or transponder was not available.

Experimental Design

The Provantis application (Instem Life Sciences Systems, Ltd.; Staffordshire, United Kingdom) was used for the direct on-line capture of most in-life data. Environmental monitoring of animal rooms (i.e., temperature/humidity and light/dark cycles) was performed using the Edstrom Watchdog system (Edstrom Industries, Inc.; Waterford, Wis.) or manually. The remainder of the data was collected manually or by the appropriate automated system.

Randomization and Group Assignment: In order to obtain groups that are comparable by body weight, all mice were assigned to their respective treatment groups using a computer-generated randomization procedure. The body weights required for randomization were determined in Week −1 (the lowest body weights were excluded from randomization). After randomization, mice were assigned to one of six groups as indicated below in Table 6:

TABLE 6

| Dose Group | Pre-Challenge Treatments | | | | Clostridium difficile Challenge | | Post-Challenge Treatments | | | No. of Mice |
|---|---|---|---|---|---|---|---|---|---|---|
| | Control Article | Dose Volume (mL) | Control Article | Dose Volume (mL) | Pathogenic Concentration | Dose Volume (mL) | Test/Control Articles | Dose Volume (mL) | Dose concentration | |
| 1 | Antibiotic Cocktail | 0.3 | Clindamycin | 0.4 | $1.0 \times 10^4$ | 0.2 | Untreated | NA | NA | 10 |
| 2 | Antibiotic Cocktail | 0.3 | Clindamycin | 0.4 | $1.0 \times 10^4$ | 0.2 | Vancomycin | 0.3 | 50 mg/kg | 10 |
| 3 | Antibiotic Cocktail | 0.3 | Clindamycin | 0.4 | $1.0 \times 10^4$ | 0.2 | Polymer Carrier | 0.3 | 62.5 mg/dose | 10 |
| 4 | Antibiotic Cocktail | 0.3 | Clindamycin | 0.4 | $1.0 \times 10^4$ | 0.2 | Sandalwood + Carrier | 0.3 | 62.5 mg/dose | 10 |
| 5 | Antibiotic Cocktail | 0.3 | Clindamycin | 0.4 | $1.0 \times 10^4$ | 0.2 | Sandalwood Oil | 0.3 | 25 mg/dose | 10 |
| 6 | Antibiotic Cocktail | 0.3 | Clindamycin | 0.4 | $1.0 \times 10^4$ | 0.2 | Sandalwood Oil | 0.3 | 50 mg/dose | 10 |

Treatment Procedure: All treatment doses were vortexed before administration to animals. On Days −6, −5 and −4, animals were administered the antibiotic cocktail via oral gavage at a volume of 0.3 mL. Treatments were administered ±1 hour from the initial day of dosing. On Day −1, animals were administered Clindamycin (10 mg/kg) via intraperitoneal (IP) at a volume of 0.4 mL. Post-challenge on Days 0-4, animals were administered the appropriate test article as listed in the table above via oral gavage at a volume of 0.3 mL. Treatments were administered ±1 hour from the initial day of dosing.

Challenge: On Day 0, mice were challenged via oral gavage with *Clostridium difficile* at a volume of 0.2 mL. The bacterial suspension was supplied (and maintained) on ice in pre filled syringes and inverted prior to administration to each group. The challenge of mice was performed in the A/BSL2 laboratory within a primary containment device. All unused challenge material was placed on ice and given to the bacteriology group for subsequent disposal by addition of bleach and subsequent autoclaving.

Fasting: Animals were not fasted during the course of the study.

Clinical Observations

Daily Observations: All mice were observed twice daily throughout the prestudy and study period for signs of mortality and moribundity.

Detailed Observations: Detailed observations were recorded daily on Days −6 through Day 11 (or more often as warranted). Clinical signs include, but are not be limited to, hypoactive, hunched posture, poor grooming, diarrhea, squinting, neurological signs, or other abnormalities.

Body Weights: Body weights for all animals were obtained during Week −1 (randomization), then daily on Days −6 through Day 11 (or more often as warranted).

Body Temperatures: Body temperatures were obtained daily on Days −6 through Day 11 (or more often as warranted).

Fecal Samples: Fecal samples for each animal were collected on Days 1-4 (or more often as warranted) for microbiology analysis (Section 11.10). An attempt was made to collect a minimum of 2 fecal pellets from each animal; if unable to collect a sample, a culture swab was used and the sample was placed in DPBS. Collected fecal samples were divided into two sterile polypropylene vials and stored at −70° C. (±10° C.). In cases where solid pellets could not be collected, external swabs of the rectum were done.

Microbiology Analysis: To isolate *C. difficile*, fecal pellets or swabs were solubilized in PBS and then cultured onto CDSA. The agar plates were then placed in the anaerobe chamber and incubated for 48-72 hours at 36° C. (±10° C.). *C. difficile* colonies were identified by colony morphology. Results were recorded as positive (for the presence of *C. difficile* in the stool) or negative.

To determine the presence of *C. difficile* toxin, fecal pellets were qualitatively assayed by enzyme inunmunoassay. To isolate *C. difficile*, the tissues were manually homogenized, serially diluted in sterile saline, plated in duplicate on *Clostridium difficile* Selective Agar (CDSA) and incubated for colony formation. The plates were counted to determine the number of CFU/tissue.

Results

As shown in Table 7, administration of sandalwood oil, alone or with a polymer carrier, resulted in decreased *C. difficile* infection as compared to untreated and placebo controls.

TABLE 7

Qualitative Fecal Pellet Analysis

| Group Number and Treatment | Animal Number | Day of Pellet Collection | | | |
|---|---|---|---|---|---|
| | | Day 1 | Day 2 | Day 3 | Day 4 |
| 1 Untreated | 1 | − | − | − | + |
| | 2 | − | − | + | + |
| | 3 | NA | NA | NA | NA |
| | 4 | − | + | + | − |
| | 5 | − | + | + | − |
| | 6 | + | + | − | − |
| | 7 | − | + | − | − |
| | 8 | − | + | − | − |
| | 9 | − | + | − | − |
| | 10 | − | + | − | − |
| 2 Vancomycin | 11 | − | − | − | − |
| | 12 | − | − | − | − |
| | 13 | − | − | − | − |
| | 14 | − | − | − | − |
| | 15 | − | + | − | − |
| | 16 | − | − | − | − |
| | 17 | − | − | − | − |
| | 18 | − | − | − | − |
| | 19 | − | − | − | − |
| | 20 | − | − | − | − |
| 3 Polymer Carrier (Placebo) | 21 | − | + | + | + |
| | 22 | + | + | + | + |
| | 23 | − | + | + | + |
| | 24 | − | + | + | + |
| | 25 | − | + | + | + |

TABLE 7-continued

Qualitative Fecal Pellet Analysis

| Group Number and Treatment | Animal Number | Day 1 | Day 2 | Day 3 | Day 4 |
|---|---|---|---|---|---|
| | 26 | − | + | + | − |
| | 27 | − | − | + | − |
| | 28 | − | + | − | − |
| | 29 | + | + | + | − |
| | 30 | − | − | − | − |
| 4 Sandalwood + Carrier | 31 | − | − | + | − |
| | 32 | − | − | − | − |
| | 33 | − | − | − | − |
| | 34 | − | − | − | − |
| | 35 | − | − | − | − |
| | 36 | − | − | + | + |
| | 37 | NA | NA | NA | NA |
| | 38 | + | + | + | − |
| | 39 | − | + | − | − |
| | 40 | − | − | + | + |
| 5 Oil (25 mg) | 41 | − | − | + | NA |
| | 42 | − | − | + | − |
| | 43 | − | − | + | + |
| | 44 | − | − | − | + |
| | 45 | − | − | + | + |
| | 46 | − | − | + | + |
| | 47 | − | − | + | + |
| | 48 | − | − | + | + |
| | 49 | − | − | − | NA |
| | 50 | − | + | + | + |
| 6 Oil (50 mg) | 51 | NA | NA | NA | NA |
| | 52 | NA | NA | NA | NA |
| | 53 | NA | NA | NA | NA |
| | 54 | NA | NA | NA | NA |
| | 55 | NA | NA | NA | NA |
| | 56 | NA | NA | NA | NA |
| | 57 | − | NA | NA | NA |
| | 58 | NA | NA | NA | NA |
| | 59 | NA | NA | NA | NA |
| | 60 | NA | NA | NA | NA |

What is claimed is:

1. A method of reducing the recurrence of a *Clostridium* infection in a subject in need thereof, comprising administering to the subject a composition comprising a therapeutically effective amount of sandalwood oil, wherein the subject is at risk for recurrence of a *Clostridium* infection.

2. The method of claim 1, wherein the infection is in the digestive tract of the subject.

3. The method of claim 1, wherein the *Clostridium* infection is a *C. difficile* infection.

4. The method of claim 1, wherein the subject has been treated with vancomycin, metronidazole or fidaxomicin.

5. The method of claim 4, wherein the composition comprising a therapeutically effective amount of sandalwood oil is administered concurrently with or subsequent to treatment with vancomycin, metronidazole or fidaxomicin.

6. The method of claim 5, wherein the composition comprising a therapeutically effective amount of sandalwood oil is administered subsequent to treatment with vancomycin, metronidazole or fidaxomicin.

* * * * *